(12) United States Patent
Kim

(10) Patent No.: US 9,757,473 B2
(45) Date of Patent: *Sep. 12, 2017

(54) CELL-PENETRATING PEPTIDE AND CONJUGATE COMPRISING SAME

(71) Applicants: GEMVAX & KAEL CO., LTD., Daejeon (KR); Sang Jae Kim, Gangnam-gu, Seoul (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,827

(22) PCT Filed: Jul. 11, 2014

(86) PCT No.: PCT/KR2014/006257
§ 371 (c)(1),
(2) Date: Jan. 8, 2016

(87) PCT Pub. No.: WO2015/005723
PCT Pub. Date: Jan. 15, 2015

(65) Prior Publication Data
US 2016/0158374 A1 Jun. 9, 2016

(30) Foreign Application Priority Data

Jul. 12, 2013 (KR) .................. 10-2013-0082265
Dec. 27, 2013 (KR) .................. 10-2013-0165071

(51) Int. Cl.
| | | |
|---|---|---|
| *A61K 31/255* | (2006.01) | |
| *A61K 31/337* | (2006.01) | |
| *A61K 47/42* | (2017.01) | |
| *A61K 47/48* | (2006.01) | |
| *A61K 38/10* | (2006.01) | |
| *C07K 7/08* | (2006.01) | |
| *C12N 9/12* | (2006.01) | |

(52) U.S. Cl.
CPC ...... *A61K 47/48246* (2013.01); *A61K 31/255* (2013.01); *A61K 31/337* (2013.01); *A61K 47/42* (2013.01); *C12N 9/1241* (2013.01); *C12N 9/1276* (2013.01); *C07K 2319/10* (2013.01); *C12Y 207/07049* (2013.01)

(58) Field of Classification Search
CPC .... A61K 31/255; A61K 31/337; A61K 47/42; A61K 47/48246; A61K 47/48; A61K 38/10; C07K 2319/10; C07K 7/08; C12N 9/1241; C12N 9/1276; C12Y 207/07049
USPC ................... 514/1.2, 21.4; 530/326
See application file for complete search history.

(56) References Cited

U.S. PATENT DOCUMENTS

| | | | |
|---|---|---|---|
| 7,030,211 B1 | 4/2006 | Gaudernack et al. | |
| 9,023,987 B2 | 5/2015 | Chung et al. | |
| 2003/0143228 A1* | 7/2003 | Chen ................. | C12N 9/1276 424/144.1 |
| 2003/0225027 A1* | 12/2003 | Huang .............. | C12Y 207/0704 514/44 R |
| 2015/0125438 A1* | 5/2015 | Kim ................... | C12N 9/1276 424/94.5 |

FOREIGN PATENT DOCUMENTS

| | | |
|---|---|---|
| JP | 2010252810 A | 11/2010 |
| KR | 20100085527 A | 7/2010 |
| KR | 20120026408 A | 3/2012 |
| WO | WO-2015005723 A1 | 1/2015 |

OTHER PUBLICATIONS

UniProt G2HEB5, pp. 1-5. Integrated into UniProtKB/TrEMBL on Nov. 16, 2011.*
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
GenBank Accession No. BAK62073.1, accessed at www.ncbi.nlm.gov/protein/BAK62073.1, create-date of Aug. 20, 2011.
International Preliminary Report on Patentability for International Application No. PCT/KR2014/006257, The International Bureau of WIPO, Switzerland, mailed on Jan. 12, 2016, 8 pages.
International Search Report for International Application No. PCT/KR2014/006257, Korean Intellecutal Property Office, Republic of Korea, mailed on Oct. 7, 2014, 12 pages.

(Continued)

*Primary Examiner* — Julie Ha
(74) *Attorney, Agent, or Firm* — Sterne, Kessler, Goldstein, Fox P.L.L.C.

(57) ABSTRACT

A cell-penetrating peptide, a conjugate of the cell-penetrating peptide with an anticancer agent, and a composition comprising the conjugate is described. An effective means for transferring a cancer-specific anticancer agent can be provided by using the cell-penetrating peptide. More particularly, by preparing the conjugate of the present invention wherein the cell-penetrating peptide and the anticancer agent are combined, the application concentration of a conventional anticancer agent can be reduced and cancer specificity can be provided, and thus an effect of reducing side effects during the treatment process can be obtained.

12 Claims, 4 Drawing Sheets

(56) References Cited

OTHER PUBLICATIONS

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Written Opinion for International Application No. PCT/KR2014/006257, Korean Intellectual Property Office, Republic of Korea, mailed on Oct. 7, 2014, 17 pages.

\* cited by examiner

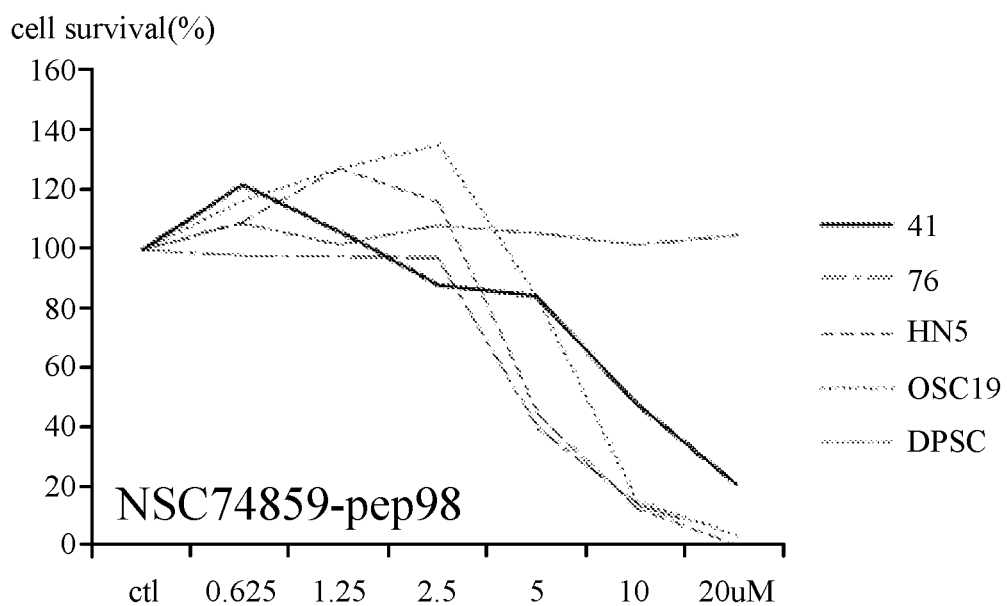

SEQUENCE LISTING

```
<160> NUMBER OF SEQ ID NOS: 2

<210> SEQ ID NO 1
<211> LENGTH: 20
<212> TYPE: PRT
<213> ORGANISM: Homo sapiens

<400> SEQUENCE: 1

Asn Arg Gly Phe Lys Ala Gly Arg Asn Met Arg Arg Lys Leu Phe Gly
1               5                   10                  15

Val Leu Arg Leu
            20

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110
```

-continued

```
Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
        290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
        450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525
```

```
Val Pro Ala Ala Glu His Arg Leu Arg Glu Ile Leu Ala Lys Phe
    530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
930                 935                 940
Asp Tyr Ser Ser Tyr Ala Arg Thr Ser Ile Arg Ala Ser Leu Thr Phe
```

-continued

```
945                950                955                960
Asn Arg Gly Phe Lys Ala Gly Arg Asn Met Arg Arg Lys Leu Phe Gly
                965                970                975

Val Leu Arg Leu Lys Cys His Ser Leu Phe Leu Asp Leu Gln Val Asn
            980                985                990

Ser Leu Gln Thr Val Cys Thr Asn Ile Tyr Lys Ile Leu Leu Leu Gln
        995                1000               1005

Ala Tyr Arg Phe His Ala Cys Val Leu Gln Leu Pro Phe His Gln
    1010                1015               1020

Gln Val Trp Lys Asn Pro Thr Phe Phe Leu Arg Val Ile Ser Asp
    1025                1030               1035

Thr Ala Ser Leu Cys Tyr Ser Ile Leu Lys Ala Lys Asn Ala Gly
    1040                1045               1050

Met Ser Leu Gly Ala Lys Gly Ala Ala Gly Pro Leu Pro Ser Glu
    1055                1060               1065

Ala Val Gln Trp Leu Cys His Gln Ala Phe Leu Leu Lys Leu Thr
    1070                1075               1080

Arg His Arg Val Thr Tyr Val Pro Leu Leu Gly Ser Leu Arg Thr
    1085                1090               1095

Ala Gln Thr Gln Leu Ser Arg Lys Leu Pro Gly Thr Thr Leu Thr
    1100                1105               1110

Ala Leu Glu Ala Ala Ala Asn Pro Ala Leu Pro Ser Asp Phe Lys
    1115                1120               1125

Thr Ile Leu Asp
    1130
```

CELL-PENETRATING PEPTIDE AND CONJUGATE COMPRISING SAME

REFERENCE TO SEQUENCE LISTING SUBMITTED ELECTRONICALLY VIA EFS-WEB

The content of the electronically submitted sequence listing (Name: 2473_0870001_SeqListing.txt; 10,387 bytes; and Date of Creation: Jan. 4, 2016) was originally submitted in the International Application No. PCT/KR2014/006257 and is incorporated herein by reference in its entirety.

FIELD OF THE INVENTION

The present invention relates to cell penetrating peptides derived from human telomerase reverse transcriptase (hTERT) enzyme, conjugates of the cell penetrating peptides, active ingredients, and compositions comprising the conjugates.

BACKGROUND

Although low molecular weight substances, nucleic acids, proteins, nano-particles, etc., have great potentials as therapeutic substances at a molecular level, their uses are limited due to the incompetence to penetrate into tissues and cell membrane. The development of a system to deliver such substances into the cell has been the active area of research over the last two decades. Transporting the substances inside the cell has been a conversation topic in a treatment of molecular method. Low-molecular weight substances, nucleic acids or nano-particles were transported inside the cell by several reagents, electroporation or heat shock. However, it was difficult to find an adequate method of delivery of proteins inside the cell without disrupting the activity and integrity of proteins. In the 1980s, in the research conducted on studying the cell penetrating capacity of HIV, it was found that HIV-TAT protein consisting of specific 11 amino acids play an important role in a process of transportation inside the cell. Thus, since 1990s, studies on finding the right method of transporting proteins inside the cell has been the intense area of research.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells.

STAT3 inhibitors regulate tumors by complexed anti-tumor mechanism including apoptosis, inhibition of angiogenesis and blockage of immune evasion. It is reported that NSC74859, which is a STAT3 inhibitor drug, has dose-dependent side effect when it is administrated. So, there is the need for the method of suppression of cancers by administrating low dose of the drug.

Paclitaxel is used for treating ovarian cancer, breast cancer, lung cancer or gastric cancer and it is reported that paclitaxel has dose-dependent side effect, which is decreases of leucocytes, erythrocytes, and thrombocytes by bone marrow suppression. So, there is the need for the method of treating cancers more efficiently by administrating low-dose paclitaxel.

DETAILED DESCRIPTION OF THE INVENTION

Technical Problem

For foods, drugs, and health supplements, transportation inside the cell is very important for the active ingredient having needs for high absorption in the body, for example, proteins, nucleic acids, peptides, lipids, glycolipids, minerals, glucose, nano-particles, biological products, contrast agents, drugs, and chemical compounds.

In case of anti-cancer drugs, for instance, it is administrated over effective dose in order to activate anti-cancer effects and it is reported that the known anti-cancer drugs have side effects for high dose administration including decrease of leucocytes, erythrocytes, thrombocytes and apoptosis of normal cells by inhibiting bone marrow. So, there is the need for the method of suppression of cancers by administrating low doses of the drug.

The objective of the present invention is to provide a cell penetrating peptide having high transmissibility inside cells and a conjugate comprising thereof.

The other objective of the present invention is to provide a conjugate which is a combination of a cell penetrating peptide and anti-cancer drugs, and a pharmaceutical composition comprising thereof as an effective means for transporting target-specific anti-cancer drugs.

The other objective of the present invention is to provide a conjugate which is a combination of a cell penetrating peptide and STAT3 inhibitors, and a pharmaceutical composition comprising thereof as an effective means for transporting STAT3 inhibitors.

The other objective of the present invention is to provide a conjugate which is a combination of a cell penetrating peptide and paclitaxel, and a pharmaceutical composition comprising thereof as an effective means for transporting paclitaxel.

Solutions for the Problem

According to the embodiment of the present invention, as a cell penetrating carrier peptide derived from telomerase, the cell penetrating carrier peptide may be provided, wherein the peptide comprises amino acid sequence of SEQ ID NO: 1, the peptide has the amino acid sequence having more than 80% homology with above-mentioned sequence, or the peptide comprises the fragment of the above-mentioned thereof.

According to the cell penetrating carrier peptide of the embodiment in the present invention, the fragment may be made of 3 or more amino acids.

According to another embodiment in the present invention, as the conjugate of the cell penetrating carrier peptide and the active ingredients, the cell penetrating carrier peptide comprising the amino acid sequence of SEQ ID NO: 1, the amino acid sequence having more than 80% homology with the above-mentioned sequence, or the peptide comprises the fragment of the above-mentioned thereof is provided.

According to another embodiment of the present invention, the active ingredients selected from the group consisting of proteins, nucleic acids, peptides, lipids, glycolipids, minerals, glucoses, nano-particles, biological products, contrast agents, drugs, chemical compounds are provided.

According to the conjugate of another embodiment in the present invention, the active ingredients may be cytokines, anti-bodies, anti-body fragments, therapeutic enzymes, soluble receptors, or ligands.

According to the conjugate of another embodiment in the present invention, the active ingredients may be for the treatment or prevention of diseases.

According to another embodiment in the present invention, a method for treating or preventing diseases comprising administering the conjugate according to the present invention to an individual in need thereof may be provided.

According to another embodiment in the present invention, a use of the conjugate according to the present invention for treatment or prevention of diseases may be provided.

According to another embodiment in the present invention, the conjugate according to the present invention for use in prevention or treatment of diseases may be provided.

According to the conjugate of another embodiment in the present invention, the diseases may be selected from the group consisting of skin diseases, pancreatic cancer, prostatic cancer, breast cancer, ovarian cancer, lung cancer, stomach cancer, hepatocellular carcinoma, epidermoid carcinoma, non-small cell lung cancer (NSCLC), skin epidermoid carcinoma, menorrhagia, endometriosis, adenomyosis, uterine fibroids, female or male infertility, precocious puberty in children, benign prostatic hyperplasia, skin diseases caused by proliferation of epidermal cells, inflammation by T-lymphocyte and combinations of above cases.

According to the conjugate of another embodiment in the present invention, the active ingredients may be anti-cancer drugs.

According to the conjugate of another embodiment in the present invention, the anti-cancer drugs may be STAT3 inhibitors.

According to the conjugate of another embodiment in the present invention, the anti-cancer drugs may be paclitaxel.

According to the conjugate of another embodiment in the present invention, the carrier peptide and the active ingredients may be connected by covalent bond, noncovalent bond, or mediation of linkers.

According to another embodiment in the present invention, a pharmaceutical composition comprising the conjugate is provided.

According to the pharmaceutical composition of another embodiment in present invention, the pharmaceutical composition may be for the treatment or prevention of diseases.

According to another embodiment in present invention, a method may be provided wherein the method comprises the step of administrating pharmaceutical composition comprising the conjugate according to the present invention to an individual in need of treatment or prevention of diseases. Specifically, the method may be for anti-cancer treatment or prevention of cancer.

According to another embodiment in present invention, use of a pharmaceutical composition comprising the conjugate according to the present invention for the treatment or prevention of disease may be provided. Specifically, the use may be for anti-cancer treatment or prevention of cancer.

According to another embodiment in the present invention, a pharmaceutical composition comprising the conjugate according to the present invention for use in treatment or prevention of diseases may be provided. Specifically, the pharmaceutical composition may be for anti-cancer treatment or prevention of cancers.

According to the pharmaceutical composition of another embodiment in present invention, the pharmaceutical composition may be for the treatment or prevention of the diseases selected from the group consisting of skin diseases, pancreatic cancer, prostatic cancer, breast cancer, ovarian cancer, lung cancer, stomach cancer, hepatocellular carcinoma, epidermoid carcinoma, non-small cell lung cancer (NSCLC), skin epidermoid carcinoma, menorrhagia, endometriosis, adenomyosis, uterine fibroids, female or male infertility, precocious puberty in children, benign prostatic hyperplasia, skin diseases caused by proliferation of epidermal cells, inflammation by T-lymphocyte and combinations of above cases.

According to the pharmaceutical composition of another embodiment in present invention, the pharmaceutical composition may be for anti-cancer treatment or prevention of cancer.

According to another embodiment in present invention, kits for transporting drugs inside cell may be provided, wherein the kits comprises the composition comprising the conjugate of the active ingredients and the cell penetrating carrier peptide comprising amino acid sequence of SEQ ID NO: 1, the peptide having more than 80% homology with above-mentioned sequence, or the peptide comprises the fragment of the above-mentioned thereof and the instruction disclosing one or more of dosage of the composition, administration routes, numbers of administration, and indication.

According to another embodiment in present invention, systems for transporting the active ingredients inside cell may be provided, as the systems for transporting the active ingredients inside cell, wherein the systems comprise the conjugate according to an embodiment in present invention, wherein the conjugate comprises amino acid sequence of SEQ ID NO: 1, the amino acid sequence having more than 80% homology with above-mentioned sequence, or the peptide comprises the fragment of the above-mentioned thereof and wherein the peptide has cell penetrability in order to transport the active ingredients into cells.

According to another embodiment in present invention, as a method for transporting active ingredients into cell by a cell penetrating carrier peptide, the method for transporting active ingredients into cell may be provided, wherein the method comprises a step for administrating the conjugate according to another embodiment in present invention in need of it, wherein the peptide comprises the amino acid sequence of SEQ ID NO: 1, the amino acid sequence having more than 80% homology with above-mentioned sequence, or the peptide comprises the fragment of the above-mentioned thereof, and wherein the peptide also has cell penetrability in order to transport the active ingredients into cells.

According to another embodiment in present invention, the method may locally transport the active ingredients to mitochondria in the cell.

According to another embodiment in present invention, polynucleotides which encode the peptide according to an embodiment in present invention are provided.

According to another embodiment in present invention, vectors which comprise the polynucleotides according to another embodiment in present invention are provided.

According to another embodiment in present invention, transformed cells which comprise the vectors according to another embodiment in present invention are provided.

According to another embodiment in present invention, the use of the cell penetrating carrier peptide according to claim 1 or claim 2 in order to transporting active ingredients into cells.

According to another embodiment in present invention, a method for treatment or prevention of diseases may be provided, wherein the method comprises administering the conjugate according to an embodiment in present invention in need of it, wherein the cell penetrating carrier peptide comprises the amino acid sequence of SEQ ID NO: 1, the amino acid sequence having more than 80% homology with above-mentioned sequence, or the fragment of the above-mentioned thereof and wherein the peptide has cell penetrability in order to transport the active ingredients into cells, wherein the diseases selected from the group consisting of skin diseases, inflammatory diseases, pancreatic cancer, prostatic cancer, breast cancer, ovarian cancer, lung cancer, stomach cancer, hepatocellular carcinoma, epidermoid carcinoma, non-small cell lung cancer (NSCLC), skin epidermoid carcinoma, menorrhagia, endometriosis, adenomyosis, uterine fibroids, female or male infertility, precocious puberty in children, benign prostatic hyperplasia, skin diseases caused by proliferation of epidermal cells, inflammation by T-lymphocyte and combinations of above cases.

Utility of the Invention

By using the cell penetrating peptide according to the present invention, the effective means to deliver cancer-specific anti-cancer drug can be provided. Specifically, by manufacturing the conjugate of the cell penetrating carrier peptide according to the present invention and anti-cancer drugs, it is provided that the effective dosage of known anti-cancer drugs can be lowered and the side effect by cancer-specific effect also can be lowered.

BRIEF DESCRIPTION OF THE DRAWINGS

FIG. 5 represents a graph for the apoptosis capability to cancer cells and normal cells after administering the conjugates of the peptide according to the present invention and NSC74859 at each concentration.

FIG. 6 represents a graph for the apoptosis capability to cancer cells and normal cells after administering a known anti-cancer drug paclitaxel only at each concentration.

BEST MODE OF EXAMINING THE INVENTION

Figure 1:
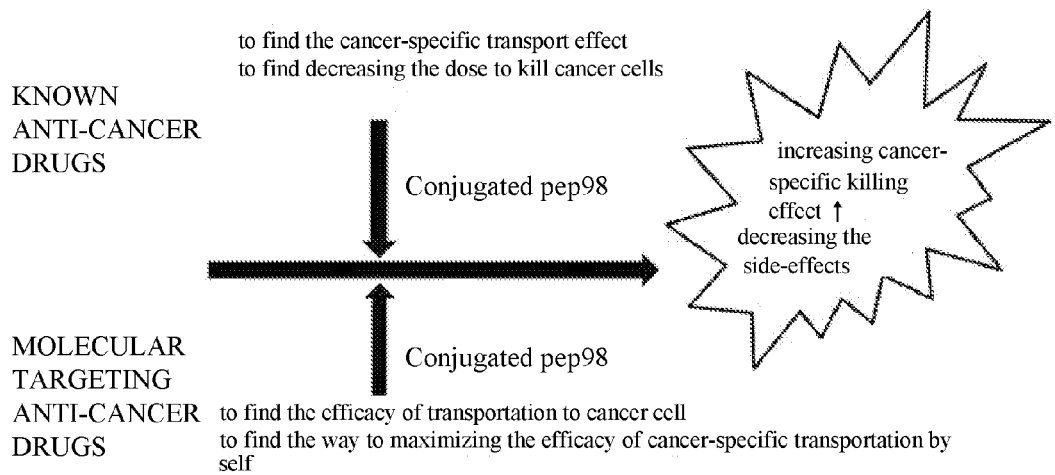
FIG. 1 represents a diagram for anti-cancer mechanism of the conjugation of the peptide according to the present invention and the known anti-cancer drugs.

The Korean patent application number 10-2013-0082265, which was filed on Jul. 12, 2013 and the Korean patent application number 10-2013-0165071, which was filed on Dec. 27, 2013 are contained within the specification of the present invention for every purpose as references. Also, this application claims the priority to the Korean patent application number 10-2013-0082265 and 10-2013-0165071, which are contained within this specification of the present invention as references.

Since the present invention can be adapted to various fields of use and in various modifications, the followings are more detailed descriptions of the present invention. Nevertheless, this is no means to limit the form of practical application; it should be understood that the intention is to include the concept and the extent of technology in all of the modifications, equivalents to alternatives. In describing the present invention, if any detailed description about the prior art is considered to deteriorate the fundamental principles of the present invention, the description will be omitted.

Proteins, nucleic acids, peptides or viruses etc. have big potentials to be used as therapeutic substances. However, their uses are limited because they cannot penetrate tissues and cell membrane due to molecular level sizes. Although, the size of molecules is small, they cannot penetrate lipid-bilayer due to structures or characteristics of the molecules. Thus, through the use of electroporation, heat shock, etc., there have been attempts to transport proteins, nucleic acids, peptides or viruses inside the cells. However, it was difficult to transfer those with neither damaging cell membranes nor keeping the active states of above molecules. There have been many studies conducted since TAT (Trans-Activating Transcriptional activator) protein derived from HIV (Human Immuno-deficiency Virus) has shown to work as a cell penetrating peptide which can transport huge active substances inside the cells. Specifically, there have been studies conducted about substances that can transport huge molecules such as proteins, nucleic acids, peptides or viruses inside the cells without causing any toxicity, unlike TAT protein which causes toxicity inside the cell. Therefore, the present invention was completed as present inventors have found that peptides derived from telomerase have outstanding efficacy as cell penetrating peptides without noticeable toxicity.

On the recently rising anti-cancer treatments, in order to replace known anti-cancer drugs which lower quality of life of patients in the treatments, efforts to find cancer-specific target molecules, which enhance growth of only cancer cells but not of normal cells, are ongoing and targeted therapies for cancer such as Gleevec, Iressa etc have been developed and used for actual clinical trials.

Thus, although continuing efforts to develop cancer-specific molecular target drugs have been made, still the known non-cancer-specific drugs such as 5-FU, Cisplatin, Doxorubicin, Docetaxel etc. are widely used in the field, so the development of delivering those non-cancer-specific drugs specifically to cancer can be another means for development of targeted molecular therapy.

In these circumstances, the development of the means for delivering the anti-cancer drugs specifically to cancer can be achieved by attaching the cytotoxic drugs to the substances which are more absorbed to cancer cells than to normal cells, combining the antibodies to cancer-specific antigens, or developing the nano-capsules which expose the anti-cancer drug when it reacts cancer-specific conditions.

By using the cell penetrating peptides according to the present invention, it is provided that the cancer-specific anti-cancer drugs are delivered effectively. Specifically, by manufacturing the conjugate of the cell penetrating peptide and the anti-cancer drugs according to the present invention, the lower side effects in the treatment can be achieved because the cancer specific effect can be done in low dosage of the known anti-cancer drugs.

STAT3 inhibitors show the effect to regulate tumors by complex anti-cancer mechanisms such as apoptosis, inhibiting angiogenesis, and immune-evasion blockage. NSC74859, one of STAT3 inhibitors, is a chemical drug, which has superior effects on cancers caused by TGF-beta signal disorder such as hepatocellular carcinoma, epidermoid carcinoma, non-small cell lung cancer (NSCLC) etc.; skin diseases by proliferation of epidermal cells, and anti-inflammation to inflammation related to T-lymphocytes.

Paclitaxel is an anti-cancer drug called by "Taxane", "antimicrotubule agent", "plant alkaloids" etc. and is made from *Taxus brevifolia*. Paclitaxel attacks cancer cells in various cell-divisional phases by specific selection of cell period. This drug is used for treatments for ovarian cancer, breast cancer, non-small cell lung cancer, skin epidermoid carcinoma by inhibiting cancer cells through inhibiting the separation and the step of separation of microtubule which is an organelle for autonomous replication during cell division.

The peptide described in this specification for the present invention is "PEP 98" of SEQ ID NO: 1 in the following Table 1. In examples of the present invention, the activity of pep 98 in comparison with pep 1 (consists of 16 amino acids) derived from telomerase was examined. SEQ ID NO: 2 lists the full length sequence of human telomerase protein. In the present specification, the term "pep" herein relates to peptides that have SEQ ID NO: 1 or, peptides comprising of amino acid sequence having more than 80% homology with the above-mentioned sequence, or fragments of the above-mentioned peptide.

TABLE 1

| SEQ ID NO | Name | Position in Telo-merase | Sequence | Length |
|---|---|---|---|---|
| 1. | pep98 | [961-980] | NRGFKAGRNMRRKLFGVLRL | 20 aa |
| 2. | Telo-merase | [1-1132] | MPRAPRCRAVRSLLRSHYREVLP LATFVRRLGPQGWRLVQRGDPAA FRALVAQCLVCVPWDARPPPAAP SFRQVSCLKELVARVLQRLCERG AKNVLAFGFALLDGARGGPPEAF TTSVRSYLPNTVTDALRGSGAWG LLLRRVGDDVLVHLLARCALFVL VAPSCAYQVCGPPLYQLGAATQA RPPPHASGPRRRLGCERAWNHSV REAGVPLGLPAPGARRRGGSASR SLPLPKRPRRGAAPEPERTPVGQ GSWAHPGRTRGPSDRGFCVVSPA RPAEEATSLEGALSGTRHSHPSV GRQHHAGPPSTSRPPRPWDTPCP PVYAETKHFPLYSSGDKEQLRPSF LLSSLRPSLTGARRLVETIFLGS RPWMPGTPRRLPRLPQRYWQMRP LFLELLGNHAQCPYGVLLKTHCP LRAAVTPAAGVCAREKPQGSVAA PEEEDTDPRRLVQLLRQHSSPWQ VYGFVRACLRRLVPPGLWGSRHN ERRFLRNTKKFISLGKHAKLSLQ ELTWKMSVRDCAWLRRSPGVGCV PAAEHRLREEILAKFLHWLMSVY VVELLRSFFYVTETTFQKNRLFF YRKSVWSKLQSIGIRQHLKRVQL RELSEAEVRQHREARPALLTSRL RFIPKPDGLRPIVNMDYVVGART FRREKRAERLTSRVKALFSVLNY ERARRPGLLGASVLGLDDIHRAW RTFVLRVRAQDPPPELYFVKVDV TGAYDTIPQDRLTEVIASIIKPQ NTYCVRRYAVVQKAAHGHVRKAF KSHVSTLTDLQPYMRQFVAHLQE TSPLRDAVVIEQSSSLNEASSGL FDVFLRFMCHHAVRIRGKSYVQC QGIPQGSILSTLLCSLCYGDMEN KLFAGIRRDGLLLRLVDDFLLVT PHLTHAKTFLRTLVRGVPEYGCV VNLRKTVVNFPVEDEALGGTAFV QMPAHGLFPWCGLLLDTRTLEVQ SDYSSYARTSIRASLTFNRGFKA GRNMRRKLFGVLRLKCHSLFLDL QVNSLQTVCTNIYKILLLQAYRF HACVLQLPFHQQVWKNPTFFLRV ISDTASLCYSILKAKNAGMSLGA KGAAGPLPSEAVQWLCHQAFLLK LTRHRVTYVPLLGSLRTAQTQLS RKLPGTTLTALEAAANPALPSDF KTILD | 1132 aa |

An embodiment of the present invention provides the polynucleotides which encodes the peptide comprising the amino acid sequence of SEQ ID NO: 1, the peptide comprising the amino acid sequence having more than 80% homology with above-mentioned sequence, or fragments of the above-mentioned peptide. By using the above polynucleotides, large amounts of the peptides can be manufactured. For example, by inserting vectors comprising the polynucleotides encoding the peptides to host cell, large amount of peptides can be manufactured.

The peptides disclosed herein may include a peptide comprising an amino acid sequence identity of above 80%, above 85%, above 90%, above 95%, above 96%, above 97%, above 98%, or above 99%. Moreover, the peptides disclosed in the present invention may include a peptide comprising SEQ ID NO: 1 or its fragments, and a peptide with more than 1 transformed/substituted amino acid, more than 2 transformed/substituted amino acids, more than 3 transformed/substituted amino acids, more than 4 transformed/substituted amino acids, more than 5 transformed/substituted amino acids, more than 6 transformed/substituted amino acid, or more than 7 transformed/substituted amino acids.

In one embodiment of the present invention, changes in amino acids include modifications of peptide's physical and chemical characteristics. For example, amino acid modification can be performed for improving thermal stability of the peptide, altering substrate specificity, and changing the optimal pH.

In an exemplary embodiment of the present disclosure, a peptide of SEQ ID NO 1, a peptide which is a fragment of the peptide of SEQ ID NO 1 or a peptide having 80% or more sequence identity with the peptides includes a peptide derived from telomerase, specifically human (*Homo sapiens*) telomerase.

The term "amino acid" herein includes not only the 22 standard amino acids that are naturally integrated into a peptide but also the D-isomers and modified amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, modification in chemical properties (e.g. 0-removing deimidation, deamidation) and structural modifications (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources. On the other hand, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, and the opposite alterations thereof. Other examples of conservative substitutions are shown in the following Table 2:

TABLE 2

| Original amino acid | Examples of residue substitution | Preferable residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |

The substantial transformation of the biological properties of peptides are performed by selecting a significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:

(1) hydrophobicity: Norleucine, met, ala, val, leu, ile;
(2) neutral hydrophilicity: cys, ser, thr;
(3) acidity: asp, glu;
(4) basicity: asn, gin, his, lys, arg;
(5) residue that affects chain orientation: gly, pro; and
(6) aromaticity: trp, tyr, phe.

Non-conservative substitutions may be performed by exchanging a member of the above classes to that of a different class. Any cysteine residues that are not related in maintaining the proper three-dimensional structure of the peptide can typically be substituted into serine, thus increasing the oxidative stability of the molecule and preventing improper cross-linkage. Conversely, improvement of stability can be achieved by adding cysteine bond(s) to the peptide.

Another type of amino acid variants of peptides are those having a changed pattern of peptide glycosylation. The term "change" herein means deletion of at least one carbohydrate residues that are found in a peptide and/or addition of at least one glycosylated residues that do not exist within a peptide.

Glycosylation in peptides are typically N-linked or O-linked. The term "N-linked" herein refers to that carbohydrate residues are attached to the side chain of asparagine residues. As tripeptide sequences, asparagine-X-serine and asparagine-X-threonine (wherein the X is any amino acid except proline) are a recognition sequence for attaching a carbohydrate residue enzymatically to the side chain of asparagine. Therefore, with the presence of one of these tripeptide sequences in a polypeptide, the potential glycosylation sites are created. "O-linked glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of a glycosylation site to a peptide is conveniently performed by changing an amino acid sequence to contain a tripeptide sequence mentioned above (for N-linked glycosylation sites). These changes may be made by addition of at least one from serine or theronine residues to the first antibody sequence, or by substitution with these residues (for O-linked glycosylation sites).

In one embodiment of the present invention, a conjugate of a peptide and an active ingredient to be transported is provided, wherein the peptide comprises amino acid sequence of SEQ ID NO: 1, the peptide is a fragment of above-mentioned peptide, or the peptide has above 80% homology with above-mentioned peptide. In one embodiment of the present invention, an active ingredient may be at least one selected from proteins, nucleic acids, peptides, lipids, glycolipids, minerals, sugars, contrast substances, drugs and chemical compounds. In one embodiment of the present invention, the active ingredients may be peptides. In one embodiment of the present invention, the active ingredients may be cytokines, antibodies, antibody fragments, therapeutic enzymes, soluble receptors, or ligands.

In the present description of present invention, "a cell penetrating peptide" disclosed herein means a peptide which can transport cargo from in vitro and/or in vivo to inside the cell. A "cargo" disclosed herein comprises all the substances that can be transported inside the cell via conjugation with a cell penetrating peptide, For example, all the substances are those which want to increase cell penetrating efficacy, specifically drugs, more specifically substances which cannot be transported inside the cell via general routes, more specifically, proteins, nucleic acids, peptides, minerals, sugars such as glucose, nano-particles, biological formulation, viruses, contrast substances or other chemical compounds, but not limited to those.

A "drug" disclosed herein is a broad concept including a substance to be transported for alleviation, prophylaxis, treatment or diagnosis of diseases, wounds, or specific symptom.

A "carrier peptide" disclosed herein is a peptide which can transport active ingredients to a targeted site via conjugation with active ingredients.

In one embodiment of the present invention, proteins or peptide as a cargo comprise one or more of hormones, hormone analogues, enzymes, enzyme inhibitors, signal transfer proteins (or peptides), antibodies and vaccines, but not limited to those. In one embodiment of the present invention, a nucleic acid is a molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA, shRNA, stRNA, snoRNA, snRNA, PNA, antisense oligomer, plasmid and other modified nucleic acids, but not limited to those. In one embodiment of the present invention, viruses comprise the whole virus or the core of virus which includes nucleic acids of the virus. In one embodiment of the present invention, a chemical substance is a broad indication comprising a natural or synthetic substance which can act as a drug.

In one embodiment of the present invention, drugs transported inside the cell by cell penetrating peptides can comprise one or more drug transporters such as liposome, micelle, nano-particles, magnetic-particles or Quantum Dot.

In one embodiment of the present invention, a cargo can be directly combined with the peptide. In another embodiment of the present invention, a cargo can be combined to the peptide via various types of bonds such as covalent or non-covalent bonds. A cargo, for example, can be combined to the N-terminal or C-terminal of the peptide in one embodiment of the present invention. For example, a cargo can be bonded to the peptide by disulfide bonds or covalent bonds. The covalent bonds are the bonds that a cargo can be bonded to α-amine of N-terminal glutamate (E), or to amine of C-terminal Lysine (K) residues. Also, a peptide and a cargo can be combined via a non-covalent bond, which can have either a peptide or a cargo can encapsulate the other as a capsule form.

In another embodiment of the present invention, a peptide can be combined with a cargo via a linker. For example, a peptide can be combined with a cargo by binding a cargo to a linker after introducing a linker such as Hynic (6-hydrazinopyridine-3-carboxylic acid) linker, to the α-amine of N-terminal glutamate, or amine of C-terminal Lysine residues.

The carrier peptide disclosed herein which is the peptide comprising amino acid sequence of SEQ ID NO: 1, or the peptide having above 80% homology of amino acid sequence with above-mentioned thereof, or a fragment of above-mentioned peptide, can be combined with a cargo at a mole fraction of 1:1, but it can be combined at mole fraction other than 1:1. For example, a mole fraction of CPP and a cargo may be more than 2:1, specifically, more than 2:1, more than 3:1, more than 4:1, more than 5:1, more than 6:1, more than 7:1, more than 8:1, more than 9:1 or more than 10:1. This means that numerous carrier peptide molecules can be combined with a cargo molecule. The numerous carrier peptide molecules can be combined in series or in parallel. "Combined in series" means that a carrier peptide and a cargo molecule are to be combined at terminal amino acids. "Combined in parallel" means that they are to be combined at a site other than terminal amino acids. On the other hand, the mole fraction of a carrier peptide and a cargo may be more than 1:2. This means that a carrier peptide molecule can be combined with numerous number of a cargo molecule. For example, a mole fraction of a carrier peptide and a cargo may be 1:2, specifically, more than 1:2, more than 1:3, more than 1:4, more than 1:5, more than 1:6, more than 1:7, more than 1:8, more than 1:9 or more than 1:10.

In one embodiment of the present invention, a use of the peptide as a drug delivery carrier to transport more than one active ingredient is provided, wherein the peptide comprises amino acid sequence of SEQ ID NO: 1, or the peptide is a fragment of above-mentioned peptide, or the peptide has above 80% homology of amino acid sequence with above-mentioned peptide.

In one embodiment of the present invention, a method of delivering drugs to a subject comprising a step of administering a composition comprising a drug and the peptide is provided; wherein the peptide comprises amino acid sequence of SEQ ID NO: 1, or the peptide is a fragment of above-mentioned peptide, or the peptide has above 80% homology of amino acid sequence with above-mentioned peptide.

In one embodiment of the present invention, a kit for drug delivery into a cell of a subject containing the composition and an instruction is provided, wherein the composition comprises a conjugate of a peptide of the invention and a drug for delivery, wherein the peptide comprises amino acid sequence of SEQ ID NO: 1 or the peptide is a fragment of above-mentioned peptide, or the peptide has above 80% homology of amino acid sequence with above-mentioned peptide, wherein the instruction includes at least one of administration dose, administration route, administration frequency, and indication of the composition.

In one embodiment of the present invention, a pharmaceutical composition having good activity to delivering active ingredients into cell and comprising the conjugate of the peptide which comprises amino acid sequence of SEQ ID NO: 1, or the peptide is a fragment of above-mentioned peptide, or the peptide has above 80% homology of amino acid sequence with above-mentioned peptide and active ingredients is provided.

In one embodiment of the present invention, the composition may contain 0.1 μg/mg to 1 mg/mg, specifically 1 μg/mg to 0.5 mg/mg, more specifically 10 μg/mg to 0.1 mg/mg of a peptide comprising amino acid sequence of at least one of SEQ ID NO: 1, a peptide comprising a amino acid sequence at least 80% sequence homology with the above-mentioned sequences, or a fragment of the above-mentioned thereof. When the peptide is contained in the above-mentioned ranges, both of safety and stability of the composition can be satisfied and the ranges are appropriate in terms of cost-effectiveness.

In one embodiment of the present invention, the composition may have applications with all animals including human, dog, chicken, pig, cow, sheep, guinea pig, and monkey.

In one embodiment of the present invention, the pharmaceutical composition may be administered through oral, rectal, transdermal, intravenous, intramuscular, intraperitoneal, in the bone marrow, epidural or subcutaneous routes.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition may be manufactured by conventional methods of the industry in the art.

In one embodiment of the present invention, the dose of the active ingredient of the medical composition may vary according to the patient's age, sex, weight, pathology and state, administration route, or prescriber's judgment. Dosage based on these factors may be determined within levels of those skilled in the art, and the daily dose, for example, may be, but not limited to, 0.1 μg/kg/day to 1 g/kg/day, specifically 1 μg/kg/day to 10 mg/kg/day, more specifically the 10 μg/kg/day to 1 mg/kg/day, more specifically the 50 μg/kg/day to 100 μg/kg/day. In one embodiment of the present invention, the pharmaceutical composition may be administered, but not limited to, 1 to 3 times a day.

The terms used herein is intended to be used to describe the embodiments, not to limit the present invention. Terms without numbers in front are not to limit the quantity but to show that there may be more than one thing of the term used. The terms "comprising", "having", "including" and "containing" shall be interpreted openly (i.e. "including but not limited to").

The reason why the numeric values are mentioned as the ranges is only because it is convenient to describe in the range rather than individual numbers. Unless otherwise noted, each individual numeric values should be understood to be described individually and integrated into the specification. Thresholds in all ranges are included and can be combined independently.

Unless otherwise noted or clearly contradicting in context, all methods mentioned herein can be performed in a proper order. The use of any one embodiment and all embodiment, or exemplary language (e.g., "such as", "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors hope that those skilled in the art can use the variations adequately and present invention be conducted in other ways than listed herein. Thus, the present invention, as allowed by the patent law, includes equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

In following examples, the cancer-specific delivering effect is verified by manufacturing the peptide (PEP98) having sequence disclosed in SEQ ID NO: 1 and the conjugate of the peptide and anti-cancer drugs.

I. Manufacturing the Peptide

Example 1

Synthesis of a peptide PEP98 and PEP1

The peptide of SEQ ID NO: 1 (PEP98) and the peptide of PEP1 for comparison were synthesized according to the conventionally known method of solid phase peptide synthesis.

More specifically, the peptide was synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to a resin were used as follows:

(NH2-Leu-2-chloro-trityl resin)

All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Asn(Trt)-OH, Fmoc-Ala-OH, Fmoc-Arg(Pbf)-OH, Fmoc-Phe-OH, Fmoc-Leu-OH, Fmoc-Lys(Boc)-OH, Fmoc-Met-OH, Fmoc-Gly-OH, Fmoc-Val-OH.

As the coupling reagents, HBTU[2-(1H-Benzotriazole-1-yl)-1,1,3,3-tetramethylaminium hexafluorophosphate]/HOBt [N-Hydroxybenzotriazole]/NMM [4-Methylmorpholine] were used.

Piperidine in 20% DMF was used to remove Fmoc. In order to remove the protection from residues or to separate the synthesized peptides from Resin, Cleavage Cocktail [TFA (trifluoroacetic acid)/TIS (triisopropylsilane)/H2O=92.5/2.5/2.5] was used.

Each peptide was synthesized by using the solid phase scaffold combined to starting amino acid with the amino acid protection, reacting the corresponding amino acids separately, washing with a solvent and deprotected, and repeating the processes.

Upon the release from the resin, the synthesized peptides were purified by HPLC, validated by Mass Spectrometry, and freeze-dried, and verified for synthesis by MS, and then freeze-dried.

Specific synthesis process of PEP 1 may be as follows:
1) Coupling

The amino acid (8 equivalent) protected with NH2-Leu-2-chloro-trityl resin, and coupling agent HBTU (8 equivalent)/HOBt (8 equivalent)/NMM (16 equivalent) melted in DMF were mixed together, and incubated at room temperature (RT) for 2 hr. Following the incubation, the reaction mixture was subjected to the sequential washes of DMF, MeOH, and DMF.

2) Fmoc Deprotection

Piperidine in 20% DMF was added and incubated at RT for 5 minutes 2 times, then sequentially washed with DMF, MeOH, and DMF.

3) Making the basic framework of peptide, NH2-N(Trt)-R(Pbf)-G-F-K(Boc)-A-G-R(Pbf)-N(Trt)-M-R(Pbf)-

K(Boc)-L-F-G-V-L-R(Boc)-L-2-chloro-trityl resin) by repeating the above mentioned-reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

The manufacturing method is based on PEP98, and PEP1 is manufactured by the same method of PEP98.

II. Intracellular Trafficking of the Cell Penetrating Peptide

Example 2

Analysis of Intracellular Trafficking of PEP98

(1) Cell Line Culture

In order to analysis of intracellular trafficking, Korean head and neck cancer cells (SNU-1041, SNU-1076), head and neck cancer cells founded by MD Anderson cancer center (OSC19, HN5), and normal cells DPSC (Dental Pulp Stem Cell) were used.

The cell lines was maintained in good condition by seeding each cells to 100 cm2-culture dishes with RPMI-1640 or DMEM culture-media, 10% FBS and antibiotic-antimycotic antibiotics and culturing in incubator (37° C., 5% CO2). The condition of cells was maintained in good condition by checking the speed and conditions of cells and sub-culturing cells per 2-5 days.

(2) Analysis of the Intracellular Trafficking of PEP98 in Head and Neck Cancer Cells by Flow Cytometry After culturing the cells with prepared cancer cells in 6 well-plate at 60-70% level 24-hours in advance, treating FITC (10 uM), pep1-FITC (10 uM), FITC-TAT (10 uM) separately, eliminating the culture media 2.5 hours later, washing with saline, and separating cells by treating Trypsin-EDTA enzyme to prepare each tube of $10^6$ cells/ml, the cells was analyzed by FACS.

After checking the results, in the case of the conjugate of PEP98 or PEP1 with FITC represent improved cell penetrability than the FITC only.

Also, at head and neck cancer cells like HN5 and OSC19 which represent lower cell penetrability of PEP1-FITC, it was confirmed that the cell penetrability of pep98-FITC is 100-200 times more than the control group and pep1-FITC.

Figure 2:
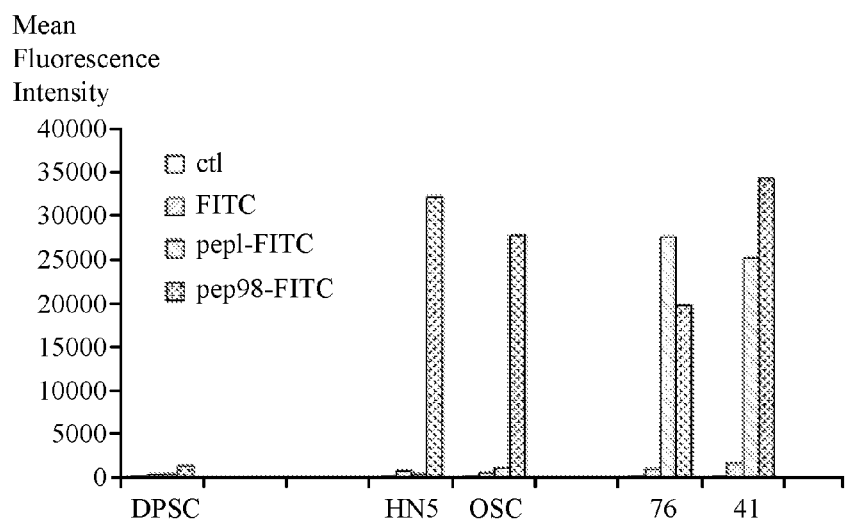
FIG. 2 represents a graph for the intracellular trafficking after administering the conjugate of the peptide according to the present invention and contrast agents (FITC).

Also, at head and neck cancer cells like SNU-1041 (marked by 41), and SNU-1076 (marked by 76) which represent the high cell penetrability of pep 1, pep98-FITC showed the same cell penetrability of pep1-FITC (See FIG. 2).

These results can show that the conjugate with pep98 always represents the high cell penetrability, that the cell penetrability of pep98 is useful through the conjugate, and that it can find the way for decreasing side-effect of anti-cancer treatment and increasing efficacy of anti-cancer treatment by the conjugation with anti-cancer drugs as active ingredients.

III. Manufacturing the Conjugate of Anti-Cancer Drugs and the Cell Penetrating Peptide

Example 3

Manufacturing the Conjugate of STAT3 Inhibitor (NSC 74859) and the Cell Penetrating Peptide (Pep98)

(1) Manufacturing the Peptide Resin of Pep98 Basic Framework for Coupling

For coupling, amino acid (8 equivalent) protected by NH2-amino-2-choloro-trityl Resin and coupling reagent HBTU (8 equivalent)/HOBt (8 equivalent)/NMM (16 equivalent) was added to the amino acid after solved in DMF, the solution was activated in 2 hours at room-temperature, and then, was rinsed sequentially with DMF, MeOH, and DMF.

After, for deprotection of Fmoc, the step of adding piperidine in 20% DMF, the step of activating at room temperature two times for 5 minutes, and the step of rinsing with DMF, MeOH, and DMF orderly were carried out.

By repeating the steps as above, the basic framework of the peptide pep98 (NH2-N(Trt)-R(Pbf)-G-F-K(Boc)-A-G-R (Pbf)-N(Trt)-M-R(Pbf)-R(Pbf)-K(Boc)-L-F-G-V-L-R (Boc)-L-2-chloro-Trityl Resin) was made.

(2) Coupling to STAT3 Inhibitor (NSC74859):

NSC 74859 (Sigma Aldrich cat.# SML0330, 4 equivalent) and coupling reagent HBTU (4 equivalent)/HOBt (4 equivalent)/NMM (8 equivalent) was added to the pep98 after solved in DMF; the solution was activated for 2 hours at room temperature; and then, rinsed sequentially with DMF, MeOH, and DMF.

To the synthetically completed peptide resin, TFA/TIS/H2O=95/2.5/2.5 was added and then, the peptide was separated from the resin.

After purification of HPLC, the peptide was lyophilized and confirmed by MS.

Example 4

Manufacturing the Conjugate of Paclitaxel and the Cell Penetrating Peptide (Pep98)

(1) Synthesizing Paclitaxel with Maleimide being Introduced

For conjugation of pep98 and paclitaxel (Sigma-Aldrich Inc., USA St Louis), the linker (4-Maleimidobutyric acid) was introduced to paclitaxel and the thiol-reactive functional group was introduced to paclitaxel.

Paclitaxel 1 g (1.17 mmol, 1 eq), 4-Maleimidobutyric acid 210 mg (1.17 mmol, 1 eq), dimethylaminopyridine (DMAP) 140 mg (2.34 mmol, 2 eq), dicyclohexylcarbodiimide (DCC) 480 mg (1.17 mmol, 1 eq) were added to 100 ml Round flask, then Methylene chloride 50 ml was added. All components were reacted at room-temperature with stirring.

The reaction was detected by TLC (Thin Layer Chromatography), and then, after the reaction was ended, distilled water (DW) 50 ml was added and worked up (Rf Value=0.43, Hexane:Ethyl acetate=1:1).

After collecting organic layers and eliminating moist by magnesium sulfide, the layers was separated by Silica gel column chromatography (Hexane:Ethyl acetate=1:1). The substances obtained from Silica gel column chromatography was concentrated and the paclitaxel with maleimide being introduced of 620 mg was obtained.

(2) Synthesizing Thiol-Modified Pep 98 (Mercaptoacetyl-Ahx-NRGFKAGRNMRRKLFGVLRL)

The peptide of SEQ ID NO: 1 (PEP98) was synthesized according to the conventionally known method of solid phase peptide synthesis. More specifically, the peptides were synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to a resin were used as follows:

(NH2-Leu-2-chloro-Trityl Resin)

All the amino acids to synthesize the peptide were protected by Fmoc at the N-terminus, and the amino acid residues were protected by Trt, Boc, t-Bu, Pbf etc. that can be dissolved in an acid. Examples include the following:

Fmoc-Asn(Trt)-OH, Fmoc-Ala-OH, Fmoc-Arg(Pbf)-OH, Fmoc-Phe-OH, Fmoc-Leu-OH, Fmoc-Lys(Boc)-OH, Fmoc-Met-OH, Fmoc-Gly-OH, Fmoc-Val-OH, Fmoc-Ahx-OH (Ahx=6-aminohexanoic acid), Fmoc-Ahx-OH was used for synthesizing peptides.

As the coupling reagents, HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used.

Piperidine in 20% DMF was used to remove Fmoc. In order to remove the protection from residues or to separate the synthesized peptides from Resin, Cleavage Cocktail [TFA (trifluoroacetic acid)/TIS (triisopropylsilane)/EDT (ethanedithiol)/TIA (TRIISOPROPHYLSILANE)/H2O=92.5/2.5/2.5/2.5] was used.

Each peptide was synthesized by using the solid phase scaffold combined to starting amino acid with the amino acid protection, reacting the corresponding amino acids separately, and then washed with a solvent and deprotected, and repeating the above steps.

Upon the release from the resin, the synthesized peptides were purified by HPLC, validated by Mass Spectrometry, and freeze-dried.

The purity of the prepared peptide was found to be 95% or higher by high-performance liquid chromatography.

Specific synthesis process may be as follows:

1) Coupling

The amino acid (8 equivalent) protected with NH2-Leu-2-chloro-Trityl Resin, and coupling agent HBTU (8 equivalent)/HOBt (8 equivalent.)/NMM (16 equivalent) melted in DMF were mixed together, and incubated at room temperature (RT) for 2 hr. Following the incubation, the reaction mixture was subjected to the sequential washes of DMF, MeOH, and DMF.

2) Fmoc Deprotection

Piperidine in 20% DMF was added and incubated at RT for 5 minutes 2 times, then sequentially washed with DMF, MeOH, and DMF.

3) Making the basic framework of peptide, Trt-Mercaptoacetyl-Ahx-N(Trt)-R(Pbf)-G-F-K(Boc)-A-G-R(Pbf)-N(Trt)-M-R(Pbf)-R(Pbf)-K(Boc)-L-F-G-V-L-R(Boc)-L-2-chloro-trityl resin) by repeating the above mentioned-reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

(3) Synthesizing the Conjugation of Paclitaxel with Maleimide being Introduced and Thiol-Modified Pep 98

1) The synthesized paclitaxel with maleimide being introduced 100 mg (98 ml, 1 eq) was solved in 1 ml DMSO.

2) The synthesized thiol-modified pep98 100 mg (48 mol, 2 eq) was solved in 1 ml DMSO and this solution was added to the solution prepared in step 1).

3) 2-3 drops of DIPEA (Diisopropyl ethyl amine) was added in the solution as above, and then, the solution was reacted at vortex for 5 minutes.

4) The end of reaction was detected by Elman reagents, and then, after disappearing the yellow color, cooling diethyl ether was added to the mixture and the compounds was settled by centrifugation.

5) After purification by Prep-HPLC and confirmation by LC/MC, the powder was made by lyophilization IV. Anti-Cancer Activity of the Conjugate of Anti-Cancer Drugs and the Cell Penetrating Peptide Example 5

Verification of Anti-Cancer Activity of the Conjugate of STAT3 Inhibitor (NSC 74859) and the Cell Penetrating Peptide (Pep98)

(1) Culturing Cell Lines

The cell line was made by the cells and the cell cultivation method described in example 2 as same.

(2) Verification of Anti-Cancer Activity

For pep98, NSC 74859, and NSC 74859-pep98 conjugate of each, the dose-dependent cell apoptosis at cancer cell lines and normal cell lines was measured.

After culturing the cancer cells and normal cells at 96 well-plate in 30-40% level 24-hours in advance by pre-seeding, treating with each reagent, and pre-evaluating killing ability by analyzing cell shape through microscope at 24 hours/48 hours/72 hours after, the quantitative analysis was done by MTT (3-(4,5-dimethylthiazol-2-yl)-2,5-diphenyltetrazolium bromide, a yellow tetrazole) assay which measures OD (optical density) values at 72 hours after.

Figure 3:
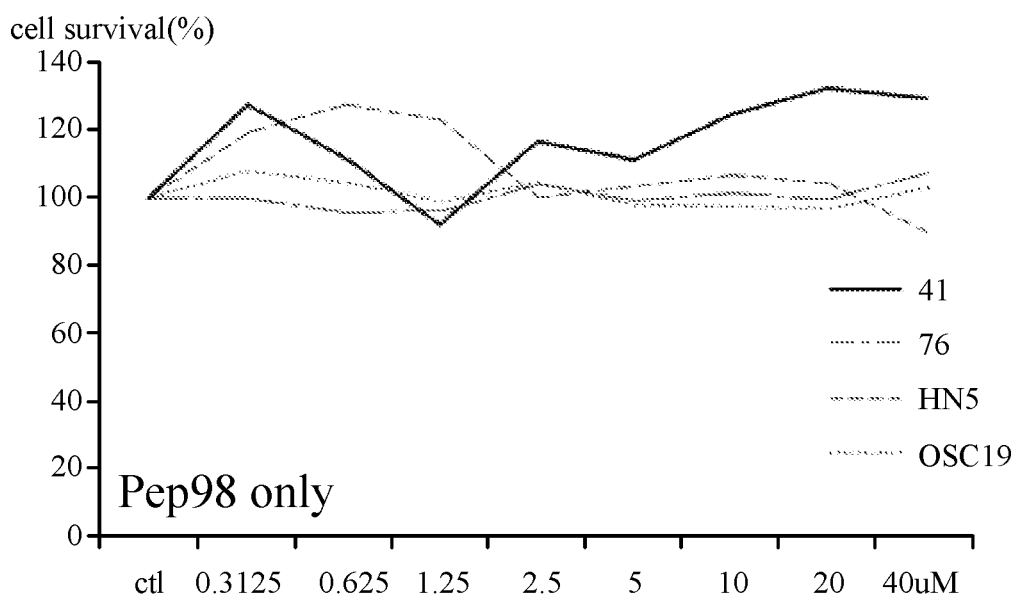
FIG. 3 represents a graph for the apoptosis capability to cancer cells and normal cells after administering the peptide according to the present invention only at each concentration.

In the case of treating pep98 only, it shows that the proliferation of cancer cells was not significantly decreased, so the pep98 does not have in itself the cytotoxicity activity for cancer cells (See FIG. 3).

Figure 4:
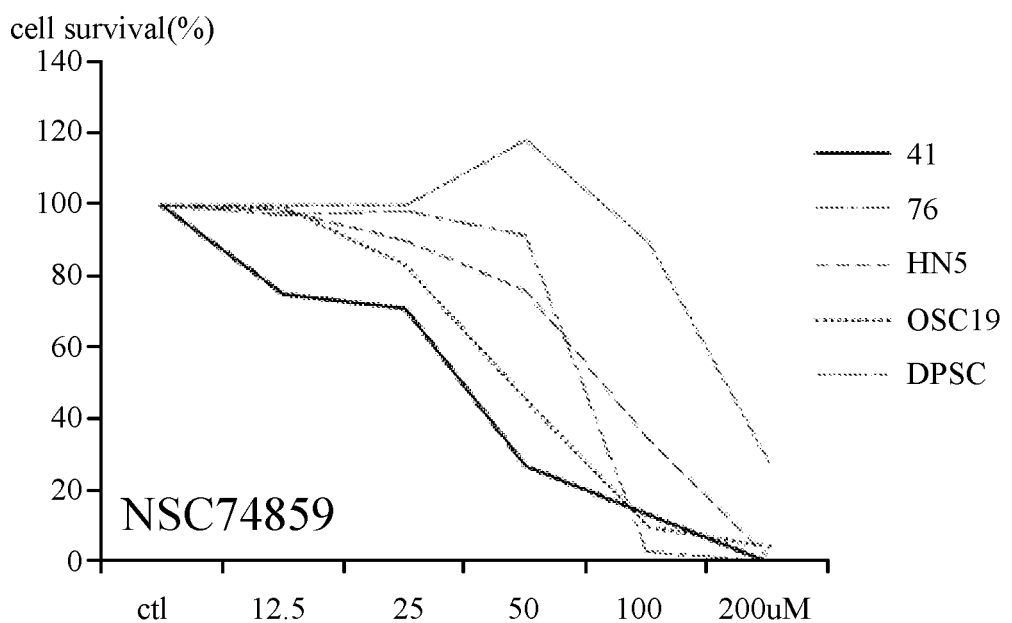
FIG. 4 represents a graph for the apoptosis capability to cancer cells and normal cells after administering the NSC74859 only as a STAT3 inhibitor at each concentration.

NSC 74859, when it treated alone, started to kill the cancer cells at head and neck cells from 50 μM concentration and kill almost the whole cancer cells at 200 μM concentration. In the case of normal cell DPSC, NSC 74859 did not kill cells till 100 μM concentration, however, the cell apoptosis was showed in 200 μM concentration (See FIG. 4).

In contrast, in the case of the pep98-NSC 74859, the cell apoptosis started to be showed at 5 μM concentration, and then, the cell apoptosis of almost the whole cancer cells at 20 μM concentration.

Also, the pep98-NSC 74859 did not kill normal cell DPSC although at the same concentration the conjugate killed almost the whole cancer cells (See FIG. 5).

Based on the results of examples as above, it was verified that the NSC 74589-pep 98 conjugate can be introduced into cancer cells specifically by being combined with pep 98, that the activity of NSC 74859 led to apoptosis of cancer cells, and that the conjugate with NSC 74859 could complete apoptosis of cancer cells in the concentration which did not lead to apoptosis of normal cells in case of DPSC (normal cell), so the conjugate according to the present invention can decrease side effects of anti-cancer drugs.

Example 6

Verification of anti-cancer activity of the conjugate of paclitaxel and the cell penetrating peptide (pep98)

(1) Culturing Cell Lines

The same cell lines and the cell cultivation method as described in example 2 were used.

(2) Verification of Anti-Cancer Activity

For paclitaxel, and for paclitaxel-pep98 conjugate, the dose-dependent cell apoptosis at cancer cell lines and normal cell lines was measured.

After preparing SNU-1041, SNU-1076, HN5, OSC-19 of each head and neck cancer cell lines in 96 well incubators, stability treatment was processed in 37° C. incubator for 24 hours. After that, paclitaxel (0 μM, 0.5 μM, 1 μM, 2 μM, 5 μM, 10 μM) and paclitaxel-pep98 conjugate (0 μM, 0.25 μM, 0.5 μM, 1 μM, 2 μM, 5 μM) were treated, MTT was treated, and after 3 hours from the treatment, the change of the cell growth ability was monitored by measuring optical density at 570 nm.

After checking the results, in all of 4 head and neck cancer cell lines (SNU-1041, SNU-1076, HN5, OSC-19), in the case of administering paclitaxel only represented apoptosis of cancer cell in the concentration from 5 to 10 μM (See FIG. 6).

Figure 7:
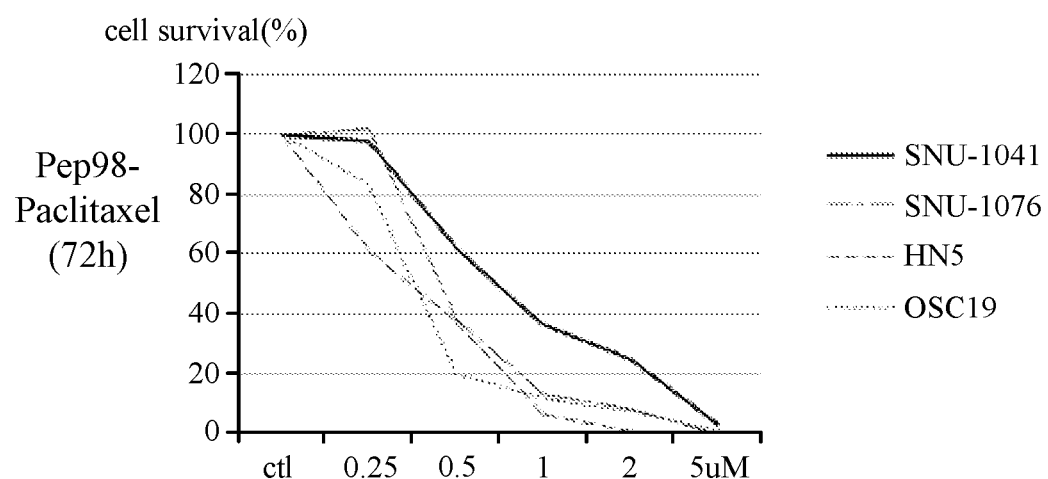
FIG. 7 represents a graph for the apoptosis capability to cancer cells and normal cells after administering the conjugates of the peptide according to the present invention and paclitaxel at each concentration.

In contrast, in all of 4 head and neck cancer cell lines (SNU-1041, SNU-1076, HN5, OSC-19), in the case of administering paclitaxel-pep98 conjugate represented apoptosis of cancer cell from the concentration at 0.5 μM (See FIG. 7).

Based on the results as above, the amount of administration of paclitaxel-pep98 conjugate which can be delivered to cancer cell specifically is smaller than these of paclitaxel solely.

All the results of the verification of anti-cancer activities according to examples as above means that the small amount of anti-cancer drugs (for example STAT3 inhibitors NSC 74859 and paclitaxel) shows anti-cancer effective by using pep 98, and by using this results decreasing the side-effects of anti-cancer drug and increasing efficiency of anti-cancer can be achieved.

Additionally, it can be predicted that, by the conjugation with pep 98, small-molecular drugs having forms of prove like NSC 74859, such as anti-inflammation drugs which targets T-lymphocytes related inflammation diseases, drugs for skin-diseases related to proliferation of epidermal cells, or drugs for anti-cancer and anti-inflammation which is extracted from natural materials like paclitaxel, shows more efficiency by improved the cell penetrability.

The invention claimed is:

1. A cell penetrating carrier peptide, wherein the carrier peptide is 20 amino acids in length and consists of the amino acid sequence of SEQ ID NO: 1.

2. A cell penetrating carrier peptide, wherein the carrier peptide is 20 amino acids in length and consists of a thiol-modified amino acid sequence of SEQ ID NO: 1.

3. The cell penetrating peptide of claim 2, wherein the thiol-modification is a mercaptoacetyl-aminohexanoic acid modification.

4. A pharmaceutical composition comprising a cell penetrating carrier peptide and an active ingredient, wherein the carrier peptide consists of the amino acid sequence of SEQ ID NO: 1.

5. The pharmaceutical composition of claim 4, wherein the active ingredient is selected from the group consisting of: proteins, nucleic acids, peptides, lipids, glycol-lipids, minerals, sugars, nano-particles, contrast agents, drugs, and chemical compounds.

6. The pharmaceutical composition of claim 5, wherein the active ingredient is selected from the group consisting of cytokines, antibodies, fragments of antibodies, therapeutic enzymes, soluble receptors and ligands.

7. The pharmaceutical composition of claim 4, wherein the active ingredient is an anti-cancer agent.

8. The pharmaceutical composition of claim 7, wherein the anti-cancer agent is a taxane or a STAT3 inhibitor.

9. The pharmaceutical composition of claim 8, wherein the tamale is paclitaxel.

10. The pharmaceutical composition of claim 8, wherein the STAT3 inhibitor is NSC74859.

11. The pharmaceutical composition of claim 4, wherein the pharmaceutical composition has cell penetrability for delivery of the active ingredient into a cell.

12. The pharmaceutical composition of claim 4, further comprising an additive selected from the group consisting of excipients, lubricants, binders, disintegrants, buffers, dispersants, surfactants, coloring agents, aromatics, and sweeteners.

* * * * *